United States Patent [19]

Nicholson

[11] Patent Number: Plant 6,305

[45] Date of Patent: Sep. 27, 1988

[54] DOGWOOD TREE "SUNSET"

[75] Inventor: Hubert A. Nicholson, Decherd, Tenn.

[73] Assignee: Commercial Nursery, Inc., Decherd, Tenn.

[21] Appl. No.: 924,516

[22] Filed: Oct. 28, 1986

[51] Int. Cl.[4] ..... A01H 5/00

[52] U.S. Cl. ..... Plt./51

[58] Field of Search ..... Plt. 51

*Primary Examiner*—Robert E. Bagwill

*Attorney, Agent, or Firm*—Frank B. Robb

[57] ABSTRACT

There is disclosed a variegated leaved red flowering Dogwood tree having purplish red blooms with distinct pinkish-red tipped new growth, olive green and yellow summer foliage with colorful fall foliage ranging from pink through red to purple.

2 Drawing Sheets

This invention relates to a new and distinct variety of variegated leaved red flowering Dogwood tree of the Cornus Florida type and is particularly noted for its purplish red blooms, the distinct pinkish-red tipped new growth, the olive green and yellow summer foliage with colorful fall foliage color ranging from pink through red to purple.

This cultivar is a branch sport discovered on the Dogwood known as "Cherokee Chief" U.S. Plant Pat. No. 1,710, which sport was found in Franklin County, Tenn. under cultivated conditions.

Asexual reproduction graft budding has established that this variety comes true, the variegated leaf margins being fixed and firm over many years of growth.

This particular cultivar is more vigorous than "Rainbow" which is the subject matter of U.S. Plant Pat. No. 2,742, when observed in the nursery growing under similar conditions. The new growth tips of pinkish-red are pronounced and in early fall, the yellow in the leaves begins to turn pinkish to red becoming darker red as fall advances.

The cultivar of my invention is notable for its vigorous growth and greater resistance to anthracnose disease which makes the cultivar distinctly different from other green-yellow variegated Dogwood trees such as Rainbow and First Lady (an unpatented variety). In addition the red blooms are distinctly different from all other known variegated Dogwood trees.

There follows a more detailed description of my new Dogwood variety, which I have designated "Sunset" as before noted, and establishes that there are substantial differences existing and provides the necessary detailed description for identification.

In the illustrations of the drawing, the same are produced by photographic means and as such subject to the possible variations which exist in that kind of an illustration, but are the best of the known illustrations available and referred to in detail in the description which is supplied, and designated in the figures as comprising the flower illustration and several stages of leaf color wherein.

DETAILED INFORMATION

Figure 1:
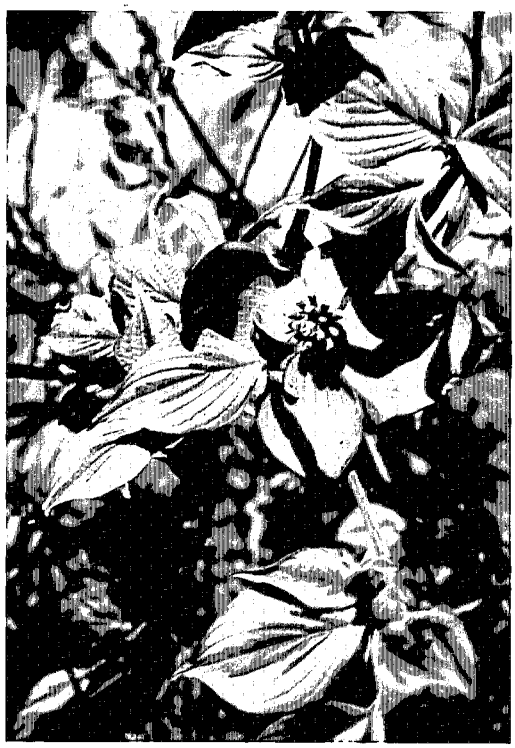
FIG. 1 shows typical bloom with early spring foliage.
Figure 2:
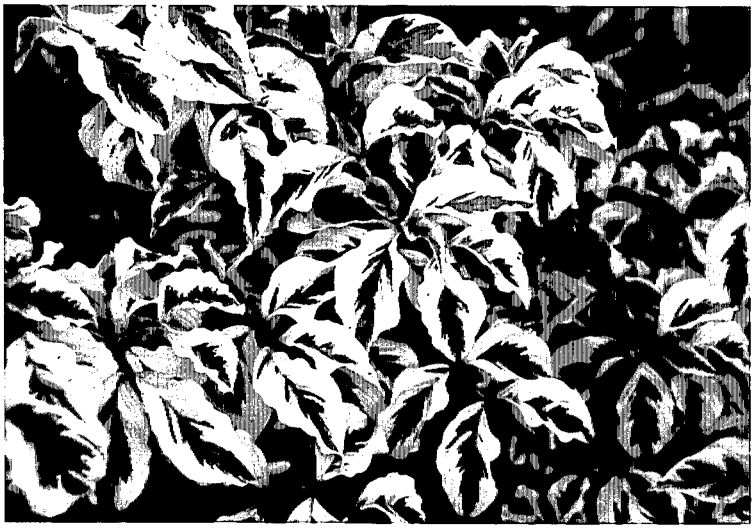
FIG. 2 shows summer foliage.
Figure 3:
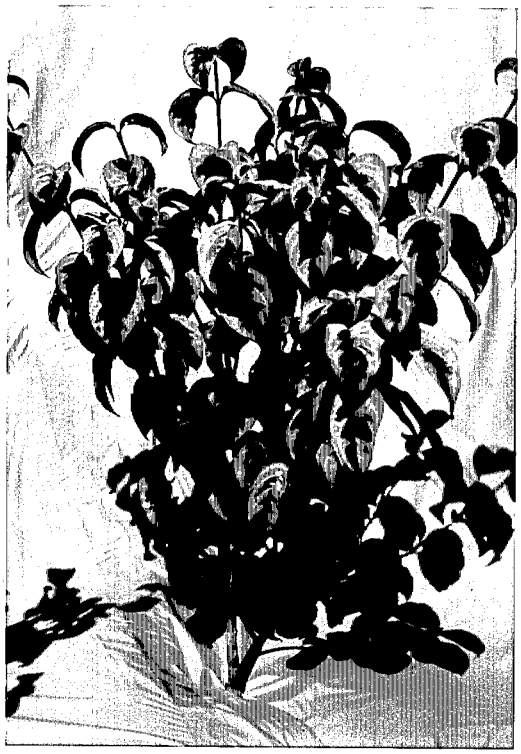
FIG. 3 illustrates the fall color on a typical branch.
Figure 4:
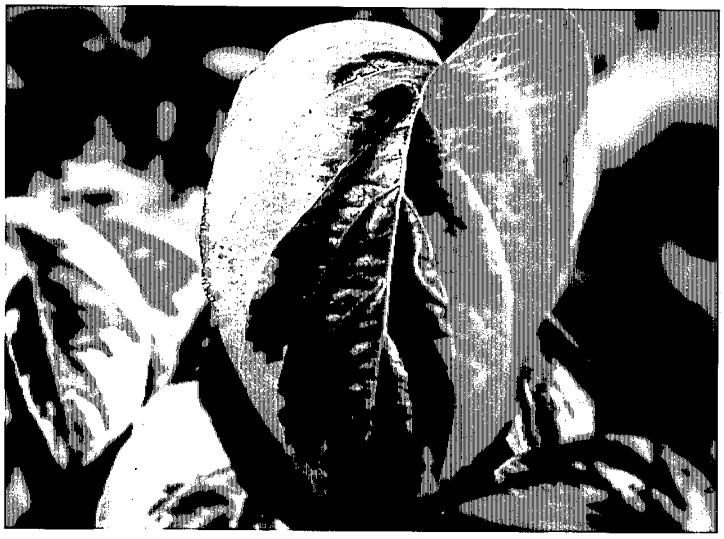
FIG. 4 shows in detail a leaf and the distinctive leaf coloration of late fall.

The specimens described were grown on property in a nursery at Franklin County, Tenn.

Parentage: Sport of mutant "Cherokee Chief" U.S. Plant Pat. No. 1,710.

Tree: Medium size: upright and spreading; tall and hardy.

*Trunk.*—Stocky and smooth.

*Branches.*—Slender and smooth.

*Color.*—Reddish brown.

Foliage:

*Leaves.*—Quantity normal: medium thickness. Length — Typical of Cornus Florida leaves in size and shape; 4 to 6 cm. long. Shape — Ovate. Color — Moderate olive green with greenish yellow margin and blotches. Margin — Smooth edge. Petiole — Medium length.

Flower buds: Hardy to zone 5.

*Size.*—Normal 0.5 to 0.75 cm.

*Shape.*—Roundish to a point in center.

*Color.*—Grayish green.

Flowers:

*Date first bloom.*—April 15–20.

*Date full bloom.*—April 18–23.

*Quantity.*—Abundant.

*Size.*—Large.

Petalage:

*Number of petals (bracts).*—4; strong purplish red.

*Shape of bracts.*—Obovate; notched.

*Size of bracts.*—Large; length 3 to 4 cm.; width 1.5 to 3 cm.

Fruits:

*When borne.*—Fall.

*Abundance.*—Average.

*Size.*—0.5 to 1 cm.; oval shape.

*Color.*—Bright red.

SUMMARY OF THE VARIOUS ASPECTS

The growth habit may be said to be very vigorous under good growing conditions and less susceptible to anthracnose disease than "Rainbow" and other pink flowering Dogwood.

The flowering habits of my new variety are similar to or very close to those of "Cherokee Chief" the bloom bracts being strong purplish red 63A (255s.p.R.) and usually 7 to 10 cm. across.

The branching habit resembles the "Cherokee Chief" the fall color of one year twigs being reddish brown.

The summer foliage is described in detail as having wide variable margins of light yellow 10A (86 brill.y.) to pale yellow 10C (96 pale g.y.) some leaves with a very faint blotch of pale pink. Mature summer colors are moderate olive green 146A (125m.ol.G.) in the center of the leaf. Blotches and blocks of various colors to the margin vary from light olive green to strong greenish yellow 151A (99s.g.Y) to brilliant greenish yellow 154B (98brill.gY).

In order to more particularly note the change in foliage from summer to fall, the fall foliage is described as being moderate olive green 146B-A, (125m.ol G.) with irregular margin of moderate yellow 162A, (87 m.Y.) with blotches of deep yellowish pink 39B, (27 deep y.Pk) to strong red 47A (12s.R). Still later fall color is moderate red 80B (15m.R) to dark red 181 for 183A (16 d.R.) with lighter color on the leaf margin. Very often fall color variations appear on the same tree as will be understood and there is a light bloom on the under side of the leaves from summer until fall color.

The overall flower color is stated to be a strong purplish red 63A (255 s.p.R.) a distinct color like that found on "Cherokee Chief".

It is to be understood that various color designations include those of The Royal Horticultural Society, with reference to color charts, and the names of the various colors are those from the National Bureau of Standard Names with the NBS color chip numbers attached.

I claim:

1. A new and distinct variety of Dogwood tree substantially as herein shown and described, characterized particularly as to novelty by the unique combination of very vigorous growth under good growing conditions, less susceptibility to anthracnose disease than other pink flowering Dogwood, strong purplish red bracts, distinct variegated foliage from the new growth tips of pinkish-red to those of early fall when the yellow in the leaves begins to turn pinkish to red, becoming darker red as fall advances, and the red bloom distinguishing the same from other known variegated Dogwood trees.

* * * * *